US008371627B2

(12) United States Patent
Chiang et al.

(10) Patent No.: US 8,371,627 B2
(45) Date of Patent: Feb. 12, 2013

(54) LATCH-BOLT MECHANISM OPERABLE TO ALLOW FOR IDLE ROTATION OF AN EXTERIOR HANDLE

(75) Inventors: Wei-Liang Chiang, Chiayi (TW); Ting-Cheng Chang, Chiayi (TW); Song-Gen Shyu, Chiayi County (TW); Ching-Chuan Kuo, Chiayi County (TW)

(73) Assignee: Tong Lung Metal Industry Co., Ltd., Chia-Yi (TW)

( * ) Notice: Subject to any disclaimer, the term of this patent is extended or adjusted under 35 U.S.C. 154(b) by 325 days.

(21) Appl. No.: 12/718,373

(22) Filed: Mar. 5, 2010

(65) Prior Publication Data

US 2010/0225126 A1    Sep. 9, 2010

(30) Foreign Application Priority Data

Mar. 6, 2009   (TW) ................................ 98203568 U (51) Int. Cl.
*E05C 1/12* (2006.01)
*E05B 13/10* (2006.01)

(52) U.S. Cl. ......... 292/164; 292/1.5; 292/169; 292/347; 70/224

(58) Field of Classification Search .................. 292/1.5, 292/163, 164, 169–169.23, 347; 70/224
See application file for complete search history.

(56) References Cited

U.S. PATENT DOCUMENTS

| | | | | |
|---|---|---|---|---|
| 1,829,815 A * | 11/1931 | Schlage | ......................... | 292/337 |
| 2,516,991 A * | 8/1950 | Heyer | ........................... | 292/244 |
| 2,661,972 A * | 12/1953 | Schlage | ......................... | 292/244 |
| 2,673,758 A * | 3/1954 | Schlage | ......................... | 292/244 |
| 2,711,920 A * | 6/1955 | Farnsworth | .............. | 292/169.13 |
| 2,733,088 A * | 1/1956 | Fisler et al. | ....................... | 292/1 |
| 2,865,666 A * | 12/1958 | Kubik | ........................... | 292/163 |
| 3,172,691 A * | 3/1965 | Russell | ......................... | 292/163 |
| 3,361,462 A * | 1/1968 | Foster | .......................... | 292/165 |
| 3,361,464 A * | 1/1968 | Foster | .......................... | 292/245 |
| 4,071,270 A | 1/1978 | Alexander | | |
| 4,108,482 A * | 8/1978 | Dietrich et al. | ............... | 292/165 |
| 4,268,075 A * | 5/1981 | Allenbaugh | .................. | 292/167 |
| 4,589,691 A | 5/1986 | Foshee et al. | | |
| 4,593,542 A * | 6/1986 | Rotondi et al. | ................. | 70/134 |
| 4,988,133 A * | 1/1991 | Shih | ............................. | 292/191 |
| 5,149,151 A * | 9/1992 | Shen | ........................... | 292/1.5 |
| 5,342,101 A * | 8/1994 | Shih | ............................. | 292/165 |
| 5,501,492 A * | 3/1996 | Kajuch | .......................... | 292/1.5 |
| 5,690,372 A * | 11/1997 | Jans | ............................. | 292/169 |
| 5,697,653 A * | 12/1997 | Aigner et al. | ...................... | 292/2 |
| 5,918,916 A * | 7/1999 | Kajuch | .......................... | 292/163 |
| 6,978,646 B2 * | 12/2005 | Raatikainen | .................... | 70/472 |
| 7,108,300 B2 * | 9/2006 | Hodgin et al. | ................ | 292/244 |
| 7,607,701 B2 * | 10/2009 | Levine | ........................... | 292/163 |
| 2010/0225123 A1 * | 9/2010 | Chiang et al. | .................. | 292/1.5 |

* cited by examiner

*Primary Examiner* — Carlos Lugo
(74) *Attorney, Agent, or Firm* — Chun-Ming Shih (57) ABSTRACT

A latch-bolt mechanism includes a housing, a latch-bolt, and a drive member. The latch-bolt is movable between an extended position and a retracted position, and includes a bolt body and an engaging member operable to move relative to the bolt body between an engagement position and a disengagement position and having an engaging portion. The drive member has a driving portion. When the engaging member is at the engagement position, the driving portion can be activated to contact and push the engaging portion so as to move the latch-bolt from the extended position to the retracted position. When the engaging member is at the disengagement position, contact between the driving portion and the engaging portion can be prevented.

10 Claims, 10 Drawing Sheets

LATCH-BOLT MECHANISM OPERABLE TO ALLOW FOR IDLE ROTATION OF AN EXTERIOR HANDLE

CROSS-REFERENCE TO RELATED APPLICATION

This application claims priority of Taiwanese Application No. 098203568, filed on Mar. 6, 2009.

BACKGROUND OF THE INVENTION

1. Field of the Invention

This invention relates to a latch-bolt mechanism, and more particularly to a latch-bolt mechanism operable to allow for idle rotation of an exterior handle.

2. Description of the Related Art

A movable door latch-bolt can be driven by a handle, a lockset, or a rotary knob to move a bolt head from an extended position to a retracted position. When the movable door latch-bolt is in a locked state, an exterior handle cannot be rotated. In this state, if a user actuates the exterior handle due to the fact that he or she does not realize the locked state, some components of the latch-bolt will be damaged, thereby reducing the service life of the latch-bolt.

SUMMARY OF THE INVENTION

The object of this invention is to provide a latch-bolt mechanism that is operable to allow for idle rotation of an exterior handle when a latch-bolt is in a locked state.

Accordingly, a latch-bolt mechanism of this invention includes a housing, a latch-bolt, and a drive member. The latch-bolt is movable between an extended position and a retracted position, and an engaging member operable to move between an engagement position and a disengagement position and having an engaging portion. The drive member has a driving portion. When the engaging member is at the engagement position, the driving portion can be activated to contact and push the engaging portion to move the latch-bolt from the extended position to the retracted position. When the engaging member is at the disengagement position, contact between the driving portion and the engaging portion can be prevented.

When the latch-bolt is in a locked state, the engaging member can be set at the disengagement position so as to allow for idle rotation of an exterior handle during operation of the exterior handle.

BRIEF DESCRIPTION OF THE DRAWINGS

These and other features and advantages of this invention will become apparent in the following detailed description of the preferred embodiments of this invention, with reference to the accompanying drawings, in which.

DETAILED DESCRIPTION OF TEE PREFERRED EMBODIMENTS

Before the present invention is described in greater detail in connection with the preferred embodiments, it should be noted that similar elements and structures are designated by like reference numerals throughout the entire disclosure.

Figure 1:
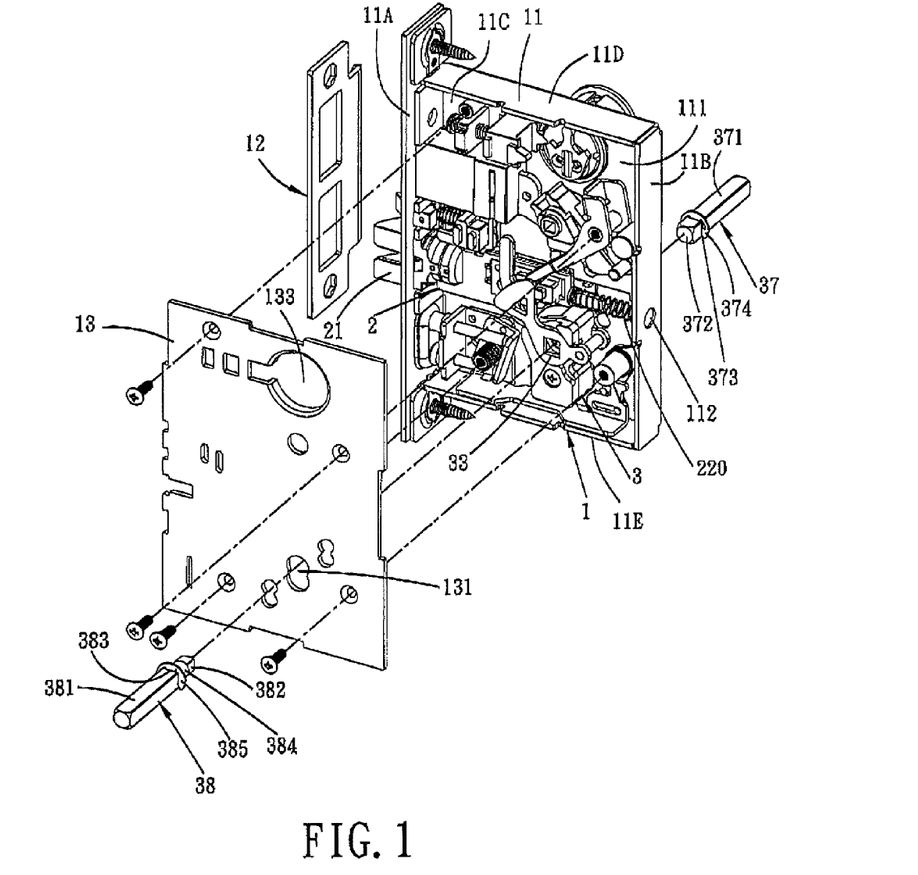
FIG. 1 is a partly exploded perspective view of the first preferred embodiment of a latch-bolt mechanism according to this invention.
Figure 2:
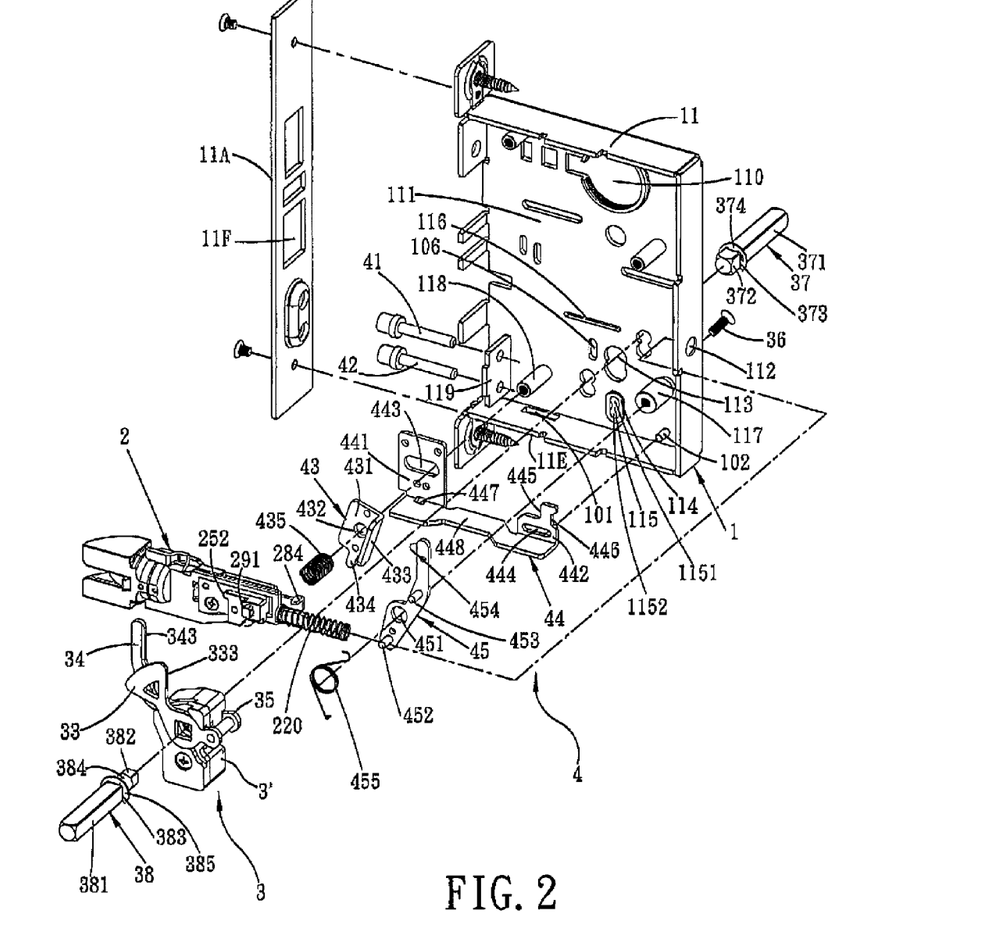
FIG. 2 is a fragmentary, partly exploded perspective view of the first preferred embodiment.

Referring to FIGS. 1 and 2, the first preferred embodiment of a latch-bolt mechanism according to this invention includes a housing 1. The housing 1 includes a housing body 11, and a cover plate 13 cooperating with the housing body 11 to define an accommodating space 111 therebetween. The housing body 11 has an outer sidewall 11A, an inner sidewall 11B formed with a spring-positioning stub member 112 projecting toward the outer sidewall 11A, and a rear wall 11C connected between rear sides of the outer and inner sidewalls 11A, 11B and formed with a loop-shaped flange 114 defining a gourd-shaped hole 115 having upper and lower hole portions 1151, 1152, a driving-rod mounting hole 113 that is gourd-shaped, a first internally threaded rod 117, a second internally threaded rod 118, amounting plate 119, a guide pin 102, a horizontal long slot 116, and a vertical slot 106. The housing body 11 further has a top wall 11D interconnecting top ends of the outer sidewall 11A, the inner sidewall 11B, and the rear wall 11C, and a bottom wall 11E interconnecting bottom ends of the outer sidewall 11A, the inner sidewall 11B, and the rear wall 11C and formed with a horizontal short slot 101. The outer sidewall 11A is formed with a bolt passage hole 11F. The cover plate 13 interconnects front sides of the outer sidewall 11A, the inner sidewall 11B, the top wall 11D, and the bottom wall 11E, and is formed with a driving-rod mounting hole 131 that is gourd-shaped and that is aligned with the driving-rod mounting hole 113 in the rear wall 11C.

Figure 3:
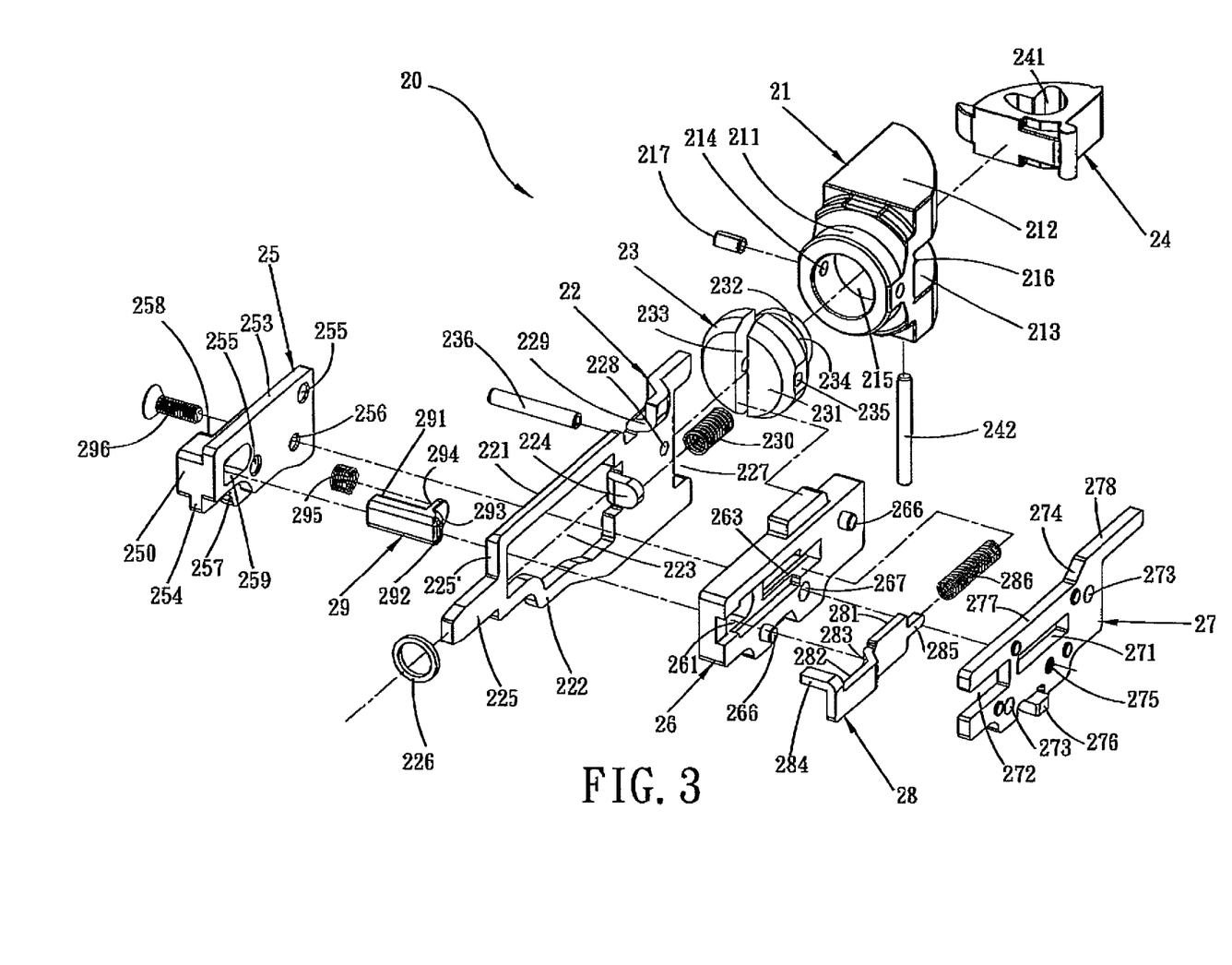
FIG. 3 is an exploded perspective view of a latch-bolt of the first preferred embodiment.
Figure 4:
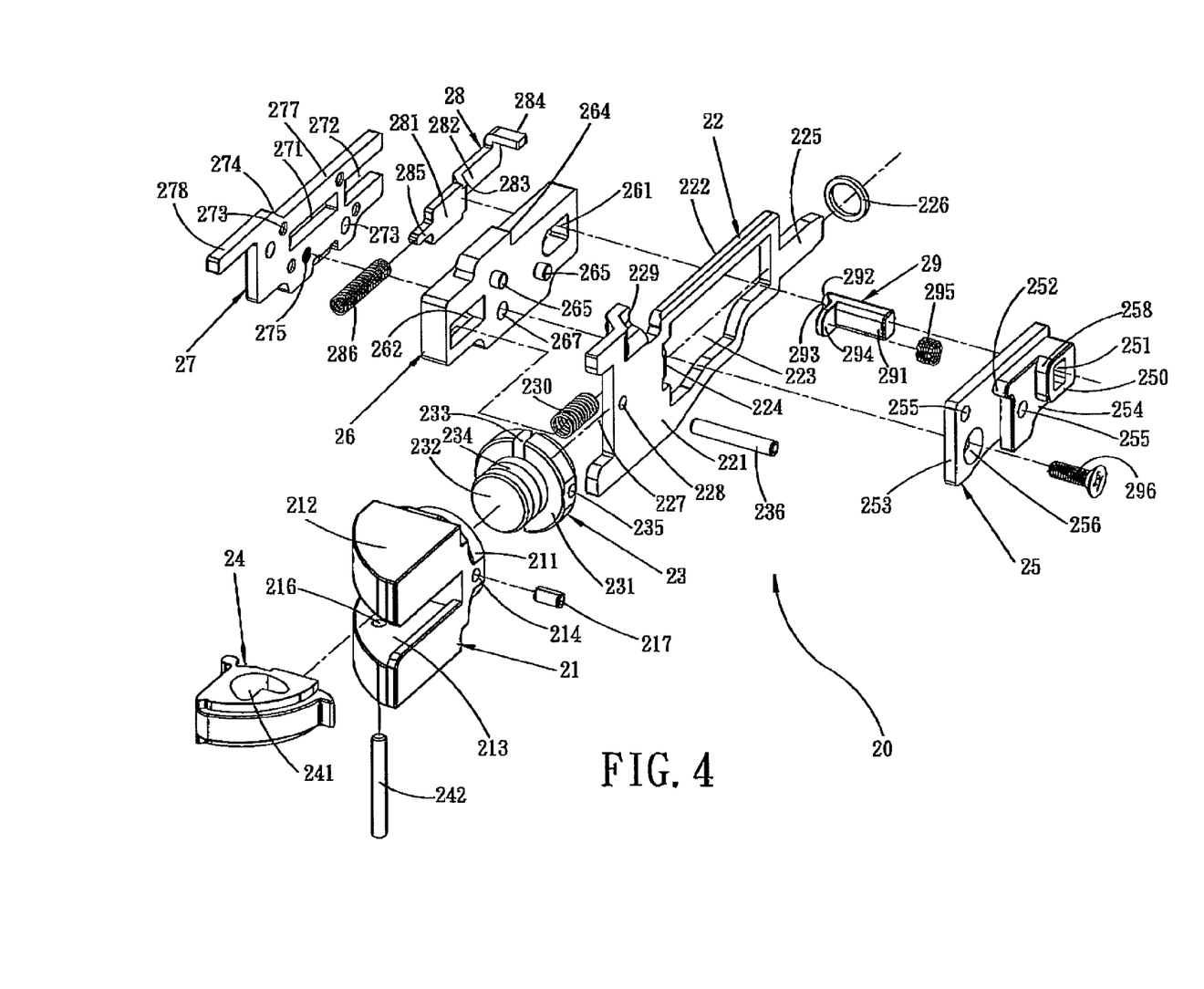
FIG. 4 is an exploded perspective view of the latch-bolt of the first preferred embodiment, viewed at another angle.

With further reference to FIGS. 3 and 4, the latch-bolt 2 includes a bolt head 21, a movable tongue member 24, a connecting member 23, a plate body 22, an engaging member 29, and a coupling device 20 for coupling the engaging member 29 to the plate body 22. The bolt head 21 is disposed at an outer end of the latch-bolt 2, and cooperates with the movable tongue member 24, the connecting member 23, and the plate body 22 to constitute a bolt body. The latch-bolt 2 is movable relative to the housing 1 between an extended position and a retracted position.

The plate body 22 has a first side surface 221, a second side surface 222 opposite to the first side surface 221, an accommodating hole 223 extending through the first and second side surfaces 221, 222 and disposed at an intermediate portion of the plate body 22, a bent portion 224 disposed at a peripheral portion of the accommodating hole 223, a recess 227 formed in an outer end of the plate body 22, a pinhole 228 adjacent to the recess 227, a pushing portion 229 adjacent to the recess 227, a projecting rod 225 disposed at an inner end of the plate body 22 and extending from a shoulder 225', and a washer 226 sleeved on the projecting rod 225 and abutting against the shoulder 225'. A coiled compression spring 220 (see FIG. 2) has an outer end sleeved on the projecting rod 225, and abuts against the washer 226, and an inner end sleeved on the spring-positioning stub member 112 of the housing 1 for biasing the latch-bolt 2 toward the extended position.

The connecting member 23 includes a large-diameter plate-connecting portion 231 and a small-diameter insert portion 232. The large-diameter plate-connecting portion 231 is formed with a slot 223 having open upper and lower ends, and a pinhole 235. The small-diameter insert portion 232 has an annular outer surface formed with an annular groove 234. An end portion of the plate body 22 defining the recess 227 is inserted into the slot 233 in the connecting member 23. A positioning pin 236 extending through the pinholes 235, 228 in the connecting member 23 and the plate body 22 for connecting the connecting member 23 fixedly to the plate body 22.

The bolt head 21 has a sleeve portion 211 and a bifurcated head portion 212. The head portion 212 has a groove 213 for receiving the movable tongue member 24, and a pinhole 216 in spatial communication with the groove 213. The movable tongue member 24 is formed with a hole 241. A pin 242 extends through the pinhole 216 in the head portion 212 and into the hole 241 in the movable tongue member 24. The sleeve portion 211 of the bolt head 21 is sleeved rotatably on the small-diameter insert portion 232 of the connecting member 23, and is formed with axially extending central hole 215 permitting the small-diameter insert portion 232 to be disposed rotatably therein, and a radially extending pinhole 214 in spatial communication with the central hole 215. A pin 217 extends through the pinhole 214 in the bolt head 21 and into the annular groove 234 in the connecting member 23 so as to prevent axial movement of the bolt head 21 relative to the connecting member 23, while allowing for rotation of the bolt head 21 relative to the connecting member 23.

The coupling device 20 includes a first coupling member 25, a second coupling member 26, a third coupling member 27, and a pushing member 28.

The first coupling member 25 includes a first plate 253 and a second plate 254 that is formed on a side surface of the first plate 253 and that has an abutment face 257 aligned with the side surface of the first plate 253. The second plate 254 further has a first driven portion 252, a projection 250 formed on a side surface thereof distal from the first plate 253 and having a second driven portion 258. The first plate 253 further includes two first coupling holes 255, a through hole 256, a first hole 251 formed through the second plate 254, and a second hole 259 formed through the first plate 253 and in spatial communication with the first hole 251. The first plate 253 is disposed within the accommodating hole 223 in the plate body 22, such that the abutment face 257 abuts against the first side surface 221 of the plate body 22.

The third coupling member 27 is configured as a plate, and is formed with a rectangular hole 271, a recess 272, two second coupling holes 273, a threaded hole 275, a bent portion 276, two horizontal surfaces 277, 278, and an inclined surface 274 connected between the horizontal surfaces 277, 278. The bent portion 276 is inserted movably into the long slot 116 (see FIG. 2) in the housing 1 for guiding the latch-bolt 2 to move horizontally.

The second coupling member 26 is also configured as a plate, and has an opening 261, a through hole 267, a first side surface facing toward the first coupling member 25 and formed with a first slot 262, and two first coupling pins 265 engaging respectively the first coupling holes 255 in the first coupling member 25 for connecting the first coupling member 25 fixedly to the second coupling member 26. The second coupling member 26 abuts against the second side surface 222 of the plate body 22. The bent portion 224 of the plate body 22 extends into the first slot 262 in the second coupling member 26. A coiled compression spring 230 is disposed in the first slot 262, and has one end abutting against a wall of the second coupling member 26 defining an end of the first slot 262, and the other end abutting against the bent portion 224 of the plate body 22. As such, the second coupling member 26 is biased by the coiled compression spring 230 toward the connecting member 23, as shown in FIG. 2. The second coupling member 26 further has a second side surface facing toward the third coupling member 27 and formed with two second coupling pins 266 and a second slot 263. The second coupling pins 266 engage respectively the second coupling holes 273 in the third coupling member 27 for connecting the third coupling member 27 fixedly to the second coupling member 26.

The pushing member 28 has a first portion 281, a second portion 282, and an inclined surface 283 disposed between the first and second portions 281, 282, and a pushed portion 284 extending from the second portion 282. The first portion 281 and a coiled compression spring 286 are disposed within the second slot 263 in the second coupling member 26. The spring 286 has one end abutting against a wall of the second coupling member 26 defining an end of the second slot 263, and the other end abutting against a stub 285 extending from the first portion 281. The first portion 281 of the pushing member 28 is disposed movably within the second slot 263 in the second coupling member 26. The second portion 282 of the pushing member 28 is disposed movably within the recess 272 in the third coupling member 27. As such, the pushing member 28 is movable relative to the housing 1 between a first position shown in FIG. 7, where the first portion 281 is aligned with the engaging member 29, and a second position shown in FIG. 8, where the second portion 282 is aligned with the engaging member 29.

Figure 7:
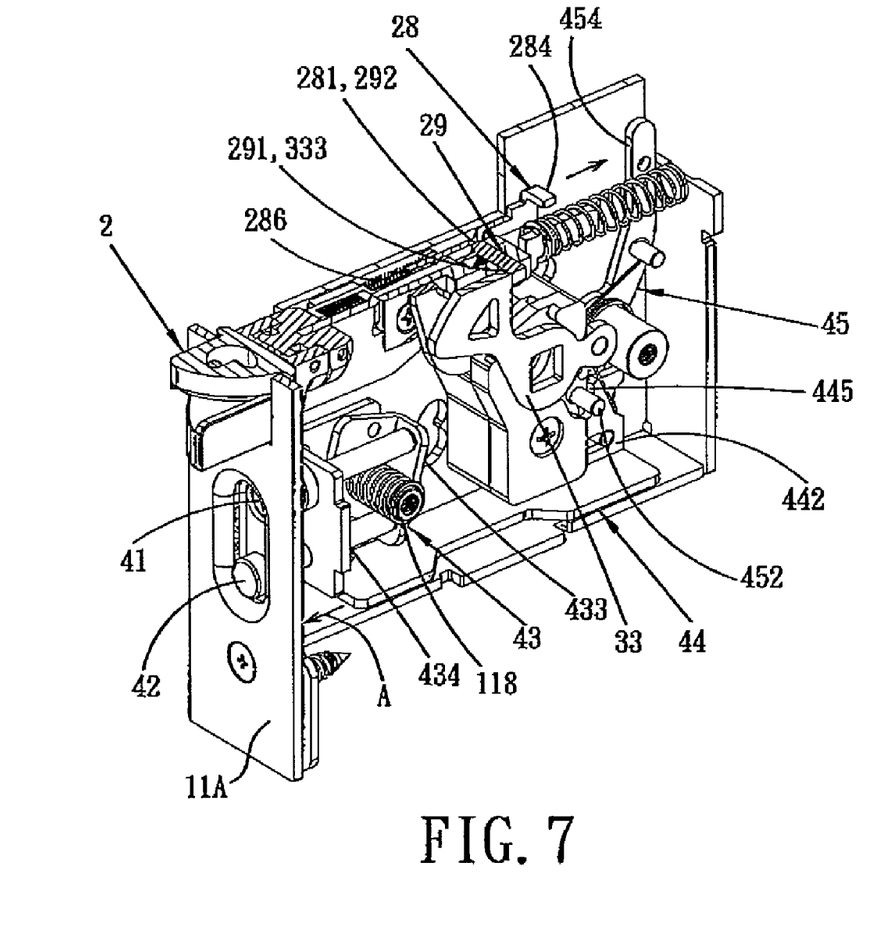
FIG. 7 is a fragmentary perspective view of the first preferred embodiment, illustrating how a first pushbutton rod is pressed to move an engaging member to an engagement position.
Figure 8:
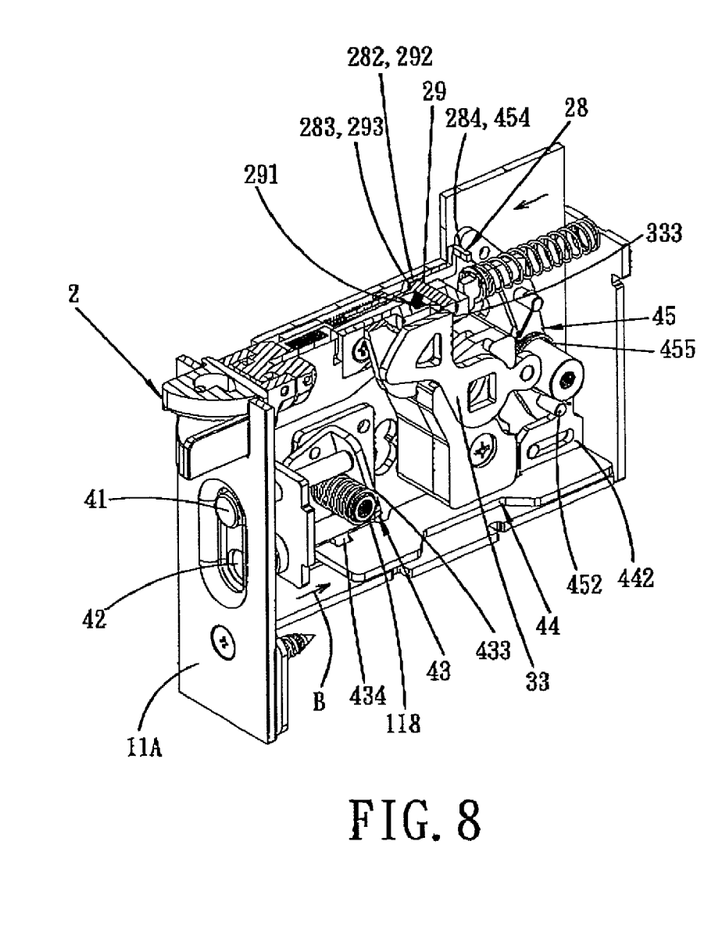
FIG. 8 is a fragmentary perspective view of the first preferred embodiment, illustrating how a second pushbutton rod is pressed to move the engaging member to a disengagement position.

The engaging member 29 is configured as a rod, and has an engaging portion 291 disposed at one end thereof, a contacting portion 292 disposed at the other end thereof, an inclined surface 293 adjacent to the contacting portion 292, and a projecting plate 294 extending along a transverse direction of the engaging member 29. The inclined surface 293 is connected between the contacting portion 292 and the projecting plate 294. The engaging member 29 extends through the first hole 251 and the second hole 259 in the first coupling member 25 and the opening 261 in the second coupling member 26. A resilient member 295 in the form of a coiled compression spring is disposed in the second hole 259 in the first coupling member 25 and the opening 261 in the second coupling member 26, and has one end abutting against a wall of the first coupling member 25 defining an end of the second hole 259, and the other end abutting against the projecting plate 294 of the engaging member 29 for biasing the contacting portion 292 of the engaging member 29 to move into contact with the pushing member 28. When the pushing member 28 is disposed at the first position, the contacting portion 292 of the engaging member 29 is in contact with the first portion 281 of the pushing member 28, as shown in FIG. 7. When the pushing member 28 is disposed at the second position, the contacting portion 292 and the inclined surface 293 of the engaging member 29 are in contact with the second portion 282 and the inclined surface 283 of the pushing member 28, respectively.

With particular reference to FIG. 2, the pushbutton device 4 is disposed in the housing 1, and includes a first pushbutton rod 41, a second pushbutton rod 42, a pushing plate 43, a movable plate 44, and a crank plate 45.

The first and second pushbutton rods 41, 42 are disposed movably on the mounting plate 119 of the housing 1.

The movable plate 44 is disposed movably in the housing 1, and includes a generally horizontal plate 448, and first and second vertical plates 441, 442 extending upwardly from a side of the generally horizontal plate 448 and having first and second guide slots 443, 444, respectively. The second internally threaded rod 118 and the guide pin 102 of the housing 1 extend respectively and movably through the first and second guide slots 443, 444 for guiding the movable plate 44 to move horizontally. The second vertical plate 442 further has a pushing portion 445 and a recess 446. A hole 447 is formed through a junction between the generally horizontal plate 448 and the first vertical plate 441.

The pushing plate 43 includes a mounting plate portion 431 formed with a pivot hole 432 permitting the second internally threaded rod 118 to extend therethrough so as to allow for rotation of the pushing plate 43 about the second internally threaded rod 118. The pushing plate 43 further includes a driven plate portion 433 connected integrally to and perpendicular to the mounting plate portion 431, and an insert rod 434 extending from a bottom side of the mounting plate portion 431 and into the hole 447 in the movable plate 44 and the short slot 101 in the housing 1. As such, the rotation of the pushing plate 43 about the second internally threaded rod 118 results in the horizontal movement of the movable plate 44. With particular reference to FIG. 7, the first pushbutton rod 41 can be pressed to contact and push a portion of the pushing plate 43 located above the second internally threaded rod 118 so as to rotate the pushing plate 43 in a first rotational direction (i.e., clockwise direction), thereby moving the movable plate 44 toward the outer sidewall 11A in a first horizontal direction (A). With particular reference to FIG. 8, the second pushbutton rod 42 can be pressed to contact and push another portion of the pushing plate 43 located below the second internally threaded rod 118 so as to rotate the pushing plate 43 in a second rotational direction (i.e., counterclockwise direction), thereby moving the movable plate 44 away from the outer sidewall 11A in a second horizontal direction (B).

With particular reference to FIGS. 2, 7, and 8, the crank plate 45 has a pivot hole 451 permitting the first internally threaded rod 117 of the housing 1 to extend therethrough so that it can rotate about the first internally threaded rod 117. The crank plate 45 includes a fist pin 452, a second pin 453, and a pushing portion 454. The first pin 452 is disposed below the pivot hole 451. The second pin 453 and the pushing portion 454 are disposed above the pivot hole 451. A torsion spring 455 is sleeved on the first internally threaded rod 117, and has one end disposed in the recess 446 in the movable plate 44 and abutting against the movable plate 44, and the other end abutting against the second pin 453 for biasing the pushing portion 454 toward the pushed portion 284 of the pushing member 28. When the movable plate 44 moves toward the outer sidewall 11A in the first horizontal direction (A), it contacts and pushes the first pin 452 to rotate the pushing portion 454 away from the pushed portion 284 of the pushing member 28 of the latch-bolt 2 against the biasing action of the torsion spring 455. Hence, the coiled compression spring 286 biases the pushing member 28 to move away from the outer sidewall 11A so that the first portion 281 of the pushing member 28 comes into contact with the contacting portion 292 of the engaging member 29, thereby pushing and moving the engaging member 29 forwardly relative to the bolt body away from the rear wall 11C of the housing 1 to an engagement position shown in FIG. 7. When the movable plate 44 moves away from the outer sidewall 11A in the second horizontal direction (B), it separates from the first pin 452, so that the pushing portion 454 is biased by the torsion spring 455 to press against the pushed portion 284 of the pushing member 28 to thereby move the pushing member 28 toward the outer sidewall 11A. Hence, the second portion 282 of the pushing member 28 comes into contact with the contacting portion 292 of the engaging member 29, so that the engaging member 29 is biased by the coiled compression spring 295 relative to the bolt body to a disengagement position shown in FIG. 8.

Figure 5:
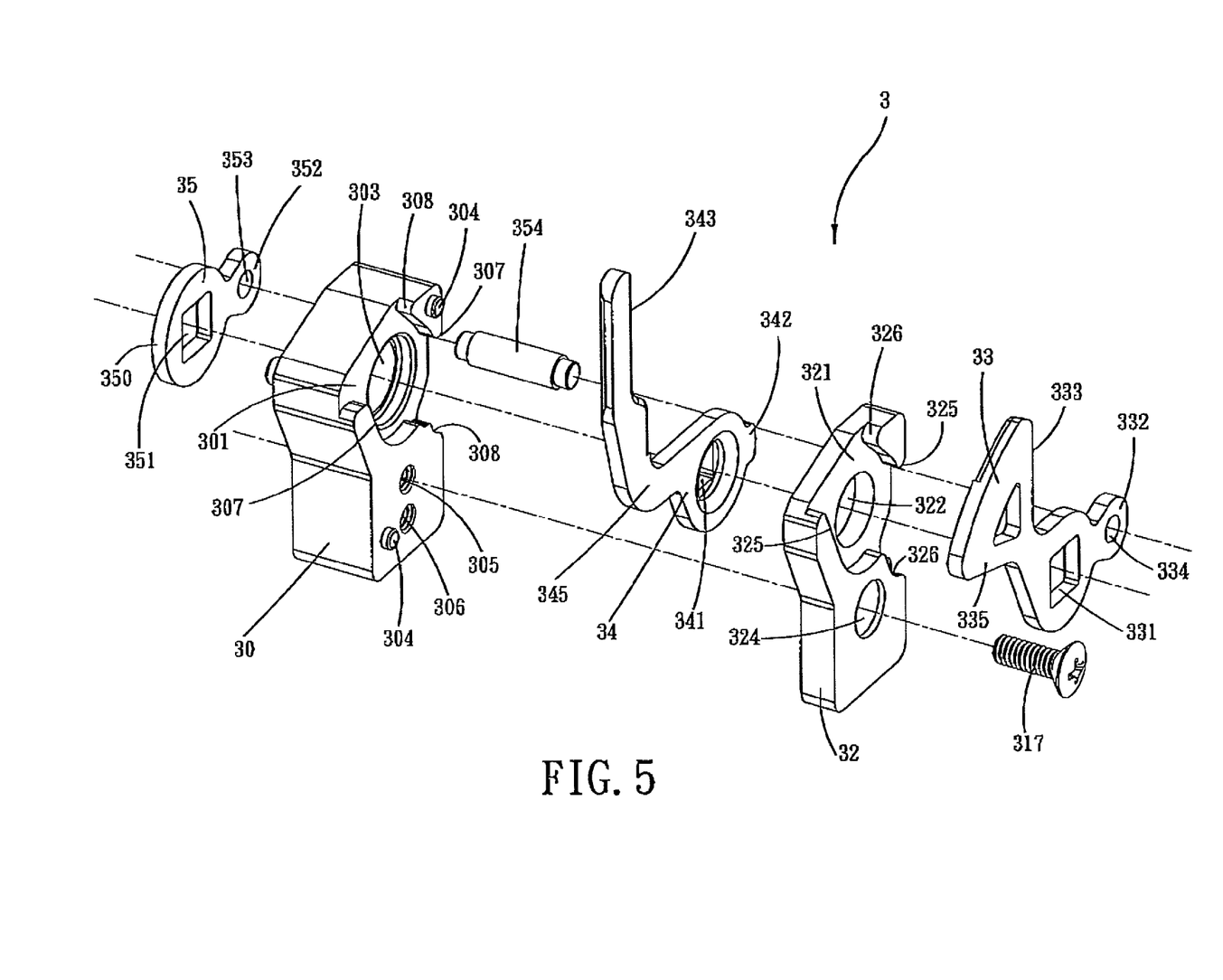
FIG. 5 is an exploded perspective view of a driving device of the first preferred embodiment.
Figure 6:
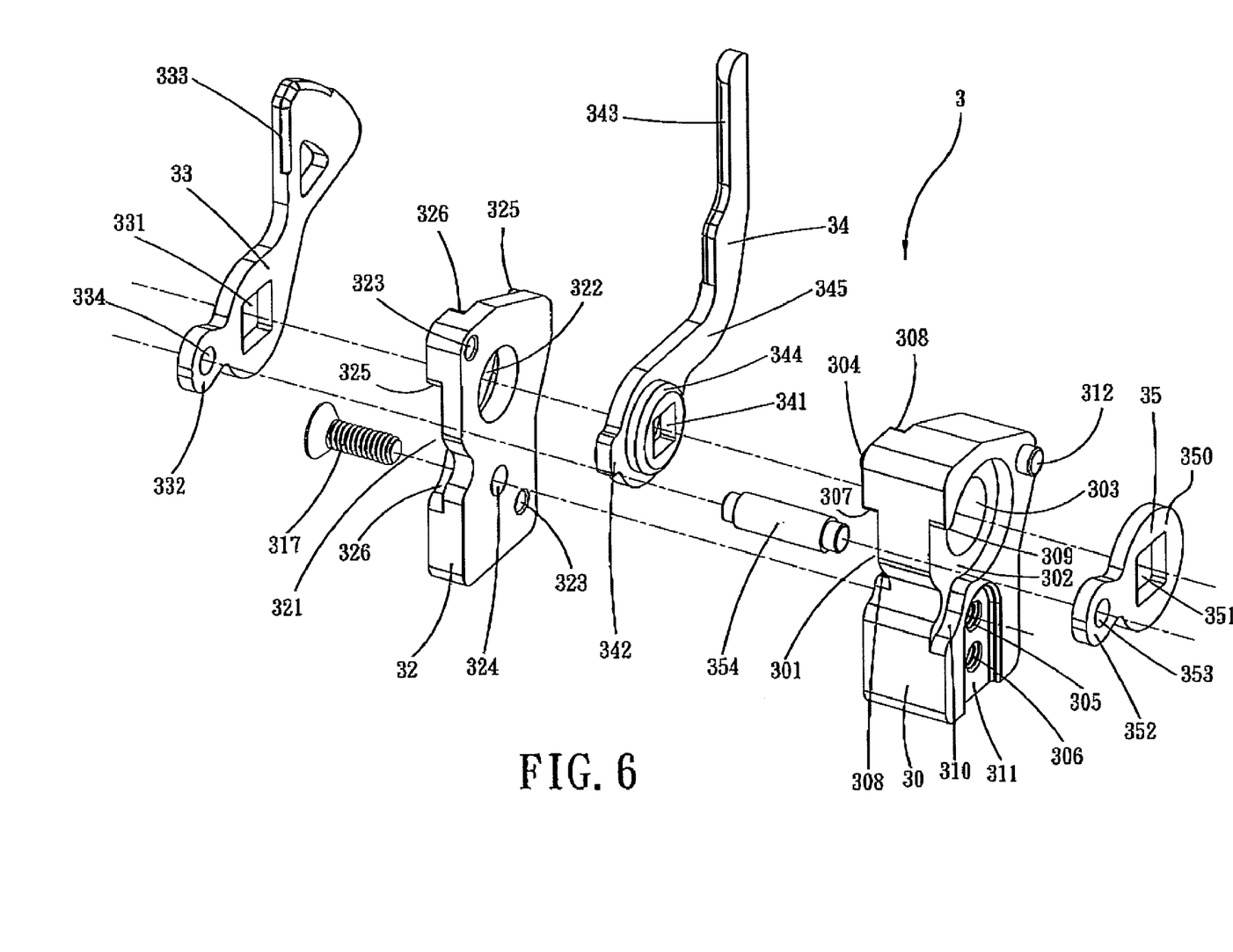
FIG. 6 is an exploded perspective view of the driving device of the first preferred embodiment, viewed at another angle.

With further reference to FIGS. 5 and 6, the driving device 3 includes a first mounting member 32, a second mounting member 30, a first drive member 33, a second drive member 34, a third drive member 35, a pin 354, and a bolt 317.

The first mounting member 32 has circular upper and lower holes 322, 324 formed therethrough. A side surface (see FIG. 5) of the first mounting member 32 has a first accommodating recess 321 in spatial communication with the upper hole 322, two first stop portions 325 adjacent to the upper hole 322 and located respectively at two sides of the upper hole 322, and two second stop portions 326 adjacent to the upper hole 322 and located respectively at two sides of the upper hole 322. An opposite side surface (see FIG. 6) of the first mounting member 32 has two pinholes 323.

The second mounting member 30 has a circular hole 303 formed therethrough, a first threaded hole 305, and a second threaded hole 306. A side surface (see FIG. 5) of the second mounting member 30 facing toward the first mounting member 32 has a second accommodating recess 301 in spatial communication with the circular hole 303, two third stop portions 307 adjacent to the circular hole 303 and located respectively at two sides of the circular hole 303, two fourth stop portions 306 adjacent to the circular hole 303 and located respectively at two sides of the circular hole 303, and two pins 304 engaging respectively the pinholes 323 in the first mounting member 32 for connecting the second mounting member 30 fixedly to the first mounting member 32. An opposite side surface (see FIG. 6) of the second mounting member 30 has a third accommodating recess 302, a slide slot 311 disposed under the third accommodating recess 302 and permitting the loop-shaped flange 114 of the housing 1 to be disposed slidably therein, a pair of fifth and sixth stop portions 309, 310 adjacent to the circular hole 303 and located respectively at two sides of the circular hole 303, and a guide pin 312 disposed slidably within the vertical slot 106 for guiding vertical movement of the second mounting member 30 relative to the housing 1. The slide slot 311 is in spatial communication with the first and second threaded holes 305, 306.

The first drive member 33 is configured as a cam, and has a portion disposed rotatably within the first accommodating recess 321 in the first mounting member 32. An end portion of the first drive member 33 has a rectangular hole 331 aligned with the upper hole 322 in the first mounting member 32, and a protrusion 332 disposed at a distal end thereof and having a pinhole 334. An opposite end portion of the first drive member 33 is configured as a swing arm 335 having a first driving portion 333. The swing arm 335 is rotatable to allow the first driving portion 333 to contact and push the engaging portion 291 of the engaging member 29 so as to move the latch-bolt 2 from the extended position to the retracted position when the engaging member 29 is disposed at the engagement position. Each of the protrusion 332 and the swing arm 335 is rotatable between the corresponding first stop portion 325 and the corresponding second stop portion 326.

The second drive member 34 is also configured as a cam, and has a portion disposed between the first and second mounting members 32, 30 and within the second accommodating recess 301 in the second mounting member 30. A lower end portion of the second drive member 34 has a rectangular hole 341 aligned with the upper hole 322 in the first mounting member 32 and the circular hole 303 in the second mounting member 30, a protrusion 342, and a loop-shaped flange 344 disposed rotatably within the circular hole 303 in the second mounting member 30 and defining the rectangular hole 341. A swing arm 345 is connected integrally to and disposed above the lower end portion of the second drive member 34, and has a second driving portion 343 that is rotatable to contact and push the first driven portion 252 of the latch-bolt 2 so as to move the latch-bolt 2 from the extended position to the retracted position. Each of the protrusion 342 and the swing arm 345 is rotatable between the corresponding third stop portion 307 and the corresponding fourth stop portion 308. As such, the first mounting member 32 is disposed between the first and second drive members 33, 34.

The third drive member 35 is configured as a rotary wheel, and has a wheel body 350 disposed rotatably within the third accommodating recess 302 in the second mounting member 30 and formed with a rectangular hole 351 at a central portion thereof, and a protrusion 352 extending outwardly from an outer periphery of the wheel body 350 and formed with a pinhole 353. The protrusion 352 is rotatable between the fifth and sixth stop portions 309, 310. As such, the second mounting member 30 is disposed between the second and third drive members 34, 35.

Figure 11:
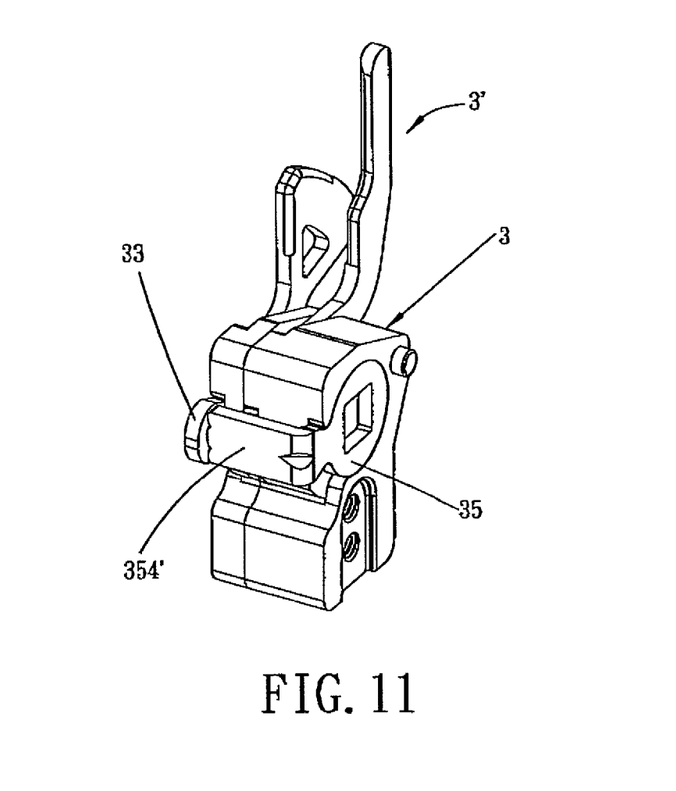
FIG. 11 is a perspective view of a driving device of the second preferred embodiment of a latch-bolt mechanism according to this invention.

A pin 354 extends through and is secured within the pinholes 334, 353 in the first and third drive members 33, 35 so as to allow for synchronous rotation of the first and third drive members 33, 35. Alternatively, the pin 354 may be replaced with a connecting plate 354' (see FIG. 11) that is connected integrally to the third drive member 35 and that is connected fixedly to the first drive member 33.

A bolt 317 extends through the lower hole 324 in the first mounting member 32 to engage the first threaded hole 305 in the second mounting member 30 so as to allow for synchronous vertical movement of the first mounting member 32, the second mounting member 30, the first drive member 33, the second drive member 34, the third drive member 35, the pin 354, and the bolt 317 relative to the housing 1. As such, a movable unit 3' (see FIG. 2) is constituted by the first mounting member 32, the second mounting member 30, the first drive member 33, the second drive member 34, the third drive member 35, the pin 354, and the bolt 317, and is movable vertically relative to the housing 1.

When the movable unit 3' is mounted to the housing 1, it can be driven to allow for relative movement of the flange 114 of the housing 1 within the slide slot 311 in the movable unit 3' and of the guide pin 312 of the movable unit 3' within the vertical slot 106 in the housing 1. As such, the movable unit 3' is movable relative to the housing 1 between first and second vertical positions. In the first vertical position, a bolt 36 can be extended fittingly through the upper hole portion 1151 of the gourd-shaped hole 115 in the housing 1 to engage the second threaded hole 306 in the movable unit 3', so as to maintain the movable unit 3' at the first vertical position. In the second vertical position, the bolt 36 can be extended fittingly through the lower hole portion 1152 of the gourd-shaped hole 115 to engage the second threaded hole 306, so as to maintain the movable unit 3' at the second vertical position.

With particular reference to FIGS. 1, 2, 9, and 10, the driving device 3 further includes a first driving rod 37 and a second driving rod 38.

Figure 9:
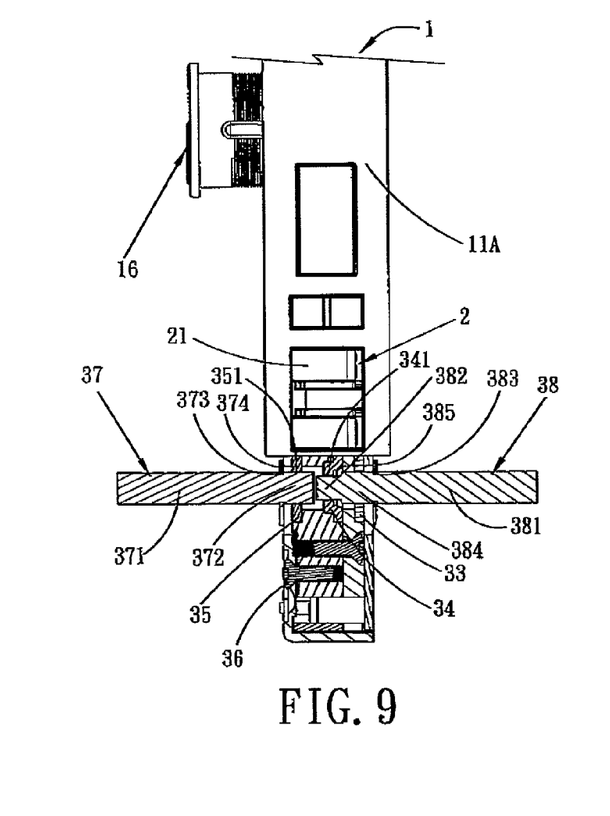
FIG. 9 is a fragmentary, partly sectional view of the first preferred embodiment, illustrating a first driving rod mounted on one end of the driving device.
Figure 10:
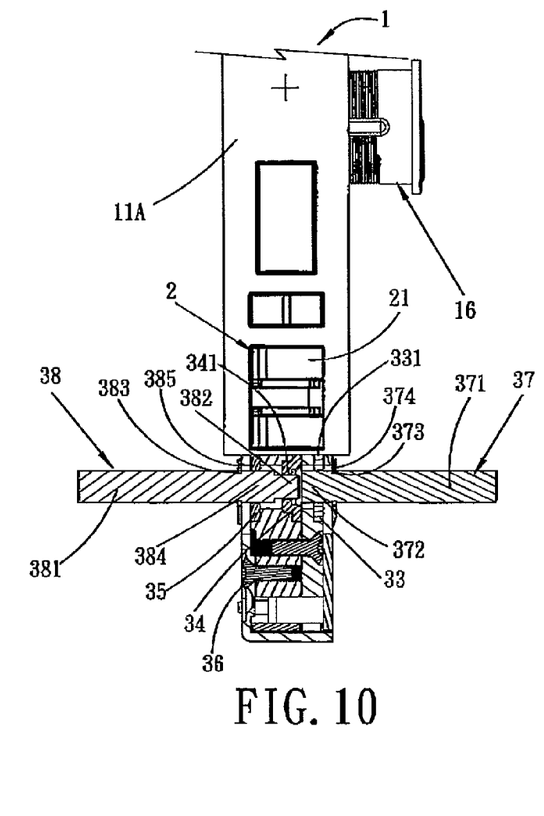
FIG. 10 is a fragmentary, partly sectional view of the first preferred embodiment, illustrating how the latch-bolt mechanism is adjusted such that the first driving rod is mounted on the other end of the driving device.

The first driving rod 37 has an outer surface formed with an annular groove 373 to divide the first driving rod 37 into a first square-cross-sectioned rod portion 371 and a second square-cross-sectioned rod portion 372. A stop ring 374 engages the annular groove 373, is sleeved fixedly on the first driving rod 37, and is adjacent to a side surface of the third drive member 35 facing away from the second mounting member 30. The first square-cross-sectioned rod portion 371 is connected fixedly to an exterior handle (not shown). The second square-cross-sectioned rod portion 372 is engaged within the rectangular hole 351 in the third drive member 35 for driving the first drive member 33 when the exterior handle is operated.

The second driving rod 38 has a third square-cross-sectioned rod portion 381, a fourth square-cross-sectioned rod portion 382, an annular groove 383 disposed between the third and fourth square-cross-sectioned rod portions 381, 382, and a circular-cross-sectioned rod portion 384 disposed between fourth square-cross-sectioned rod portion 382 and the annular groove 383. A stop ring 385 engages the annular groove 383, is sleeved fixedly on the second driving rod 38, and is adjacent to a side surface of the first drive member 33 facing away from the first mounting member 32. The third square-cross-sectioned rod portion 381 is connected fixedly to an interior handle (not shown). The circular-cross-sectioned rod portion 384 is disposed within the rectangular hole 331 in the first drive member 33. The fourth square-cross-sectioned rod portion 382 is engaged within the rectangular hole 341 in the second drive member 34 for driving the second drive member 34 when the interior handle is operated.

In an alternative embodiment, the first mounting member 32, the second mounting member 30, the third drive member 35, the pin 354, the bolt 317 can be omitted from the driving device 3, and each of first and second drive members 33, 34 is formed with an integral pivot pin disposed rotatably within a pivot hole in the housing 1. Due to the omission of the third drive member 35, it is necessary for the first and second driving rods 37, 38 to change in construction for driving rotation of the first and second drive members 33, 34, respectively.

With particular reference to FIGS. 2, 7 and 8, the pushbutton mechanism 4 is operable to determine whether or not the latch-bolt 2 can be driven by the exterior handle.

When the first pushbutton rod 41 is pressed to rotate the pushing plate 43 clockwise, due to engagement between the insert rod 434 and the hole 447, the movable plate 44 is moved toward the outer sidewall 11A. Hence, the pushing portion 445 pushes the first pin 452 to rotate the pushing portion 454 away from the pushed portion 284 of the pushing member 28, so that the pushing member 28 is biased by the coiled compression spring 286 to move away from the outer sidewall 11A, thereby resulting in contact between the first portion 281 of the pushing member 28 and the contacting portion 292 of the engaging member 29, which leads to movement of the engaging member 29 to the engagement position. In the engagement position, as shown in FIG. 7, contact between the first driving portion 333 of the first drive member 33 and the engaging portion 291 of the engaging member 29 is allowed, so that the latch-bolt 2 can be driven by the exterior handle.

When the second pushbutton rod 42 is pressed to rotate the pushing plate 43 counterclockwise, due to engagement between the insert rod 434 and the hole 447, the movable plate 44 is moved away from the outer sidewall 11A. Hence, the pushing portion 445 separated from the first pin 452 to allow the pushing portion 454 to be biased by the torsion spring 455 to press against the pushed portion 284 of the pushing member 28, so that the pushing member 28 is moved toward the outer sidewall 11A, thereby resulting in contact between the second portion 282 of the pushing member 28 and the contacting portion 292 of the engaging member 29, which leads to movement of the engaging member 29 to the disengagement position. In the disengagement position, as shown in FIG. 8, contact between the first driving portion 333 of the first drive member 33 and the engaging portion 291 of the engaging member 29 is prevented, so that the latch-bolt 2 cannot be driven by the exterior handle. In this state, idle rotation of the exterior handle occurs when the exterior handle is driven.

With particular reference to FIG. 9, in this embodiment, the exterior handle and a lockset 16 are disposed on a first side surface of the housing 1. When movement of the exterior handle and the lockset 16 from the first side surface of the housing 1 onto a second side surface of the housing 1 to allow connection between the first coupling rod 37 and the interior handle and between the second coupling rod 38 and the exterior handle is desired, with particular reference to FIG. 10, it is only necessary to rotate the bolt head 21 relative to the connecting member 23 (see FIG. 3) by 180° and adjust simply the positions of the first and second driving rods 37, 38 such that the second square-cross-sectioned rod portion 372 of the first driving rod 37 is engaged within the rectangular hole 331 in the first drive member 33 and the circular-cross-sectioned rod portion 384 of the second driving rod 38 extends through the rectangular hole 351 in the third drive member 35. As a result, the first driving rod 37 is moved from one end of the driving device 3 to the other end of the driving device 3. In this state, the first and second drive members 33, 34 can also be driven by the first and second driving rods 37, 38, respectively.

Figure 12:
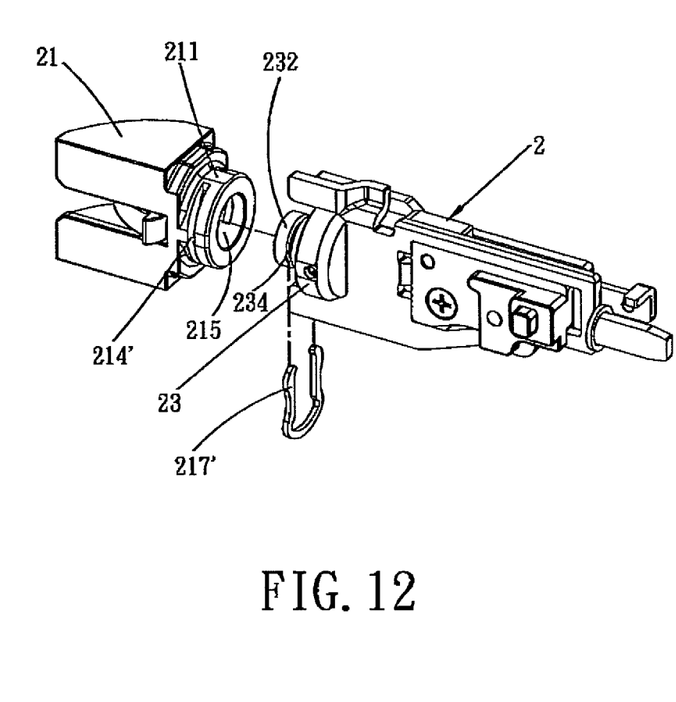
FIG. 12 is a partly exploded perspective view of a latch-bolt of the third preferred embodiment of a latch-bolt mechanism according to this invention.

FIG. 12 shows a modified latch-bolt 2 of another preferred embodiment of a latch-bolt mechanism according to this invention. In this embodiment, the connecting member 23 of the modified latch-bolt 2 has an insert portion 232 that is formed with an annular groove 234 in an annular outer surface thereof. The bolt head 21 of the modified latch-bolt 2 has a sleeve portion 211 that is sleeved rotatably on the insert portion 232 of the connecting member 23, and that is formed with an axially extending central hole 215 permitting the insert portion 232 to be disposed rotatably therein, and an opening 214' in spatial communication with the central hole 215. The modified latch-bolt 2 further includes a retaining ring 217' extending through the opening 214' in the bolt head 21 and into the annular groove 234 in the connecting member 23 so as to prevent axial movement of the bolt head 21 relative to the connecting member 23, while allowing for rotation of the bolt head 21 relative to the connecting member 23.

With this invention thus explained, it is apparent that numerous modifications and variations can be made without departing from the scope and spirit of this invention. It is therefore intended that this invention be limited only as indicated by the appended claims.

We claim:

1. A latch-bolt mechanism comprising:
   a housing;
   a latch-bolt movable relative to said housing between an extended position and a retracted position and including a bolt body that is disposed movably on said housing, an engaging member that is operable to move on said bolt body between an engagement position and a disengagement position and that has an engaging portion, and a coupling device that connects said bolt body to said engagement member; and
   a driving device including a first drive member disposed in said housing and having a first driving portion, said first driving portion of said first drive member being activated to contact and push said engaging portion of said engaging member so as to move said latch-bolt from the extended position to the retracted position when said engaging member is disposed at the engagement position, contact between said first driving portion of said first drive member and said engaging portion of said engaging member being prevented when said engaging member is disposed at the disengagement position;
   wherein:
   said bolt body includes a plate body disposed in said housing;
   said coupling device includes first, second, and third coupling members, and a pushing member that is disposed movably on said plate body, that is in contact with said engaging member, and that is activatable to allow for movement of said engaging member between the engagement position and the disengagement position, said pushing member cooperating with said first, second, and third coupling members to connect said bolt body to said engagement member, said second coupling member being formed with a slot, said pushing member being disposed on said slot of said second coupling member; and
   wherein said driving device further includes:
      a first mounting member disposed in said housing and permitting said first drive member to be disposed thereon;
      a second mounting member disposed in said housing;
      a second drive member disposed between said first and second mounting members such that said first mounting member is disposed between said first and second drive members;
      a third drive member disposed on said second mounting member such that said second mounting member is disposed between said second and third drive members;
      a first driving rod extending through either said first or third drive member for driving synchronous rotation of said first and third drive members; and
      a second driving rod extending through said second drive member for driving rotation of said second drive member.

2. The latch-bolt mechanism as claimed in claim 1, wherein said coupling device of said latch-bolt further includes a resilient member for biasing said engaging member to contact said pushing member.

3. The latch-bolt mechanism as claimed in claim 2, wherein said pushing member has a first portion and a second portion, said engaging member having a contacting portion biased by said resilient member to move into contact with said first portion of said pushing member when said engaging member is disposed at the engagement position and with said second portion of said pushing member when said engaging member is disposed at the disengagement position, said latch-bolt mechanism further comprising a pushbutton device that is in operational contact with said pushing member between a first pushing position, making said first portion to be aligned with said engagement member to allow movement of said latch-bolt, and a second pushing position, moving said pushing member to allow said second portion to be aligned with said engagement member, preventing movement of said latch-bolt.

4. The latch-bolt mechanism as claimed in claim 3, wherein said pushbutton device includes:
a pushing plate disposed pivotally in said housing;
a first pushbutton rod disposed movably in said housing and operable to rotate said pushing plate in a first rotational direction;
a second pushbutton rod disposed movably in said housing and operable to rotate said pushing plate in a second rotational direction opposite to the first rotational direction;
a movable plate disposed movably in said housing, said movable plate being driven by said pushing plate to move in a first horizontal direction when said pushing plate is rotated in the first rotational direction, said movable plate being driven by said pushing plate to move in a second horizontal direction when said pushing plate is rotated in the second rotational direction; and
a crank plate disposed pivotally in said housing and having a pushing portion biased toward said pushing member of said latch-bolt, said pushing portion of said crank plate being rotated by said movable plate away from said pushing member of said latch-bolt such that said first portion of said pushing member is biased to contact said contacting portion of said engaging member when said movable plate is moved in the first horizontal direction, said pushing portion of said crank plate being biased to rotate to thereby contact and move said pushing member of said latch-bolt such that said second portion of said pushing member comes into contact with said contacting portion of said engaging member when said movable plate is moved in the second horizontal direction.

5. The latch-bolt mechanism as claimed in claim 4, wherein said pushbutton device further includes a torsion spring for biasing said pushing portion of said crank plate to contact and move said pushing member of said latch-bolt such that said second portion of said pushing member comes into contact with said contacting portion of said engaging member when said movable plate is moved in the second horizontal direction.

6. The latch-bolt mechanism as claimed in claim 1, wherein said latch-bolt further includes a driven portion, and said second drive member of said driving device has a second driving portion that is rotatable in said housing to contact and push said driven portion to thereby move said latch-bolt from the extended position to the retracted position.

7. The latch-bolt mechanism as claimed in claim 6, wherein said latch-bolt includes:
a connecting member having an insert portion, said insert portion having an annular outer surface formed with an annular groove;
a bolt head having a sleeve portion that is sleeved rotatably on said insert portion of said connecting member and that is formed with an axially extending central hole permitting said insert portion of said connecting member to be disposed rotatably therein, and a radially extending pinhole in spatial communication with said central hole; and
a pin extending through said pinhole in said bolt head and into said annular groove in said connecting member so as to prevent axial movement of said bolt head relative to said connecting member.

8. The latch-bolt mechanism as claimed in claim 1, wherein said latch-bolt includes:
a connecting member having an insert portion, said insert portion having an annular outer surface formed with an annular groove;
a bolt head having a sleeve portion that is sleeved rotatably on said insert portion of said connecting member and that is formed with an axially extending central hole permitting said insert portion of said connecting member to be disposed rotatably therein, and an opening in spatial communication with said central hole; and
a retaining ring extending through said opening in said bolt head and into said annular groove in said connecting member so as to prevent axial movement of said bolt head relative to said connecting member.

9. A latch-bolt mechanism comprising:
a housing;
a latch-bolt movable relative to said housing between an extended position and a retracted position and including a bolt body that is disposed movably on said housing, an engaging member that is operable to move on said bolt body between an engagement position and a disengagement position and that has an engaging portion, and a coupling device connecting said bolt body to said engagement member and including first, second, and third coupling members, and a pushing member having a first portion and a second portion, said pushing member being movable on said bolt body such that said engaging member is moved into contact with said first portion of said pushing member when said engaging member is disposed at the engagement position and with said second portion of said pushing member when said engaging member is disposed at the disengagement position, said pushing member cooperating with said first, second, and third coupling members to connect said bolt body to said engagement member, said second coupling member being formed with a slot, said pushing member being disposed on said slot of said second coupling member;
a pushbutton device that is in operational contact with said pushing member between a first pushing position, making said first portion to be aligned with said engagement member to allow movement of said latch-bolt, and a second pushing position, moving said pushing member to allow said second portion to be aligned with said engagement member, preventing movement of said latch-bolt; and
a driving device including a first drive member disposed in said housing and having a first driving portion, said first driving portion of said first drive member being activated to contact and push said engaging portion of said engaging member so as to move said latch-bolt from the extended position to the retracted position when said engaging member is disposed at the engagement position, contact between said first driving portion of said first drive member and said engaging portion of said engaging member being prevented when said engaging member is disposed at the disengagement position;
wherein said driving device further includes:
a first mounting member disposed in said housing and permitting said first drive member to be disposed thereon;
a second mounting member disposed in said housing;
a second drive member disposed between said first and second mounting members such that said first mounting member is disposed between said first and second drive members;

a third drive member disposed on said second mounting member such that said second mounting member is disposed between said second and third drive members;

a first driving rod extending through either said first or third drive member for driving synchronous rotation of said first and third drive members; and a second driving rod extending through said second drive member for driving rotation of said second drive member.

10. A latch-bolt mechanism comprising:

a housing;

a latch-bolt movable relative to said housing between an extended position and a retracted position and including a bolt body that is disposed movably on said housing, an engaging member that is operable to move on said bolt body between an engagement position and a disengagement position and that has an engaging portion, and a coupling device connecting said bolt body to said engagement member and including first, second, and third coupling members, and a pushing member movable on said bolt body, and a resilient member for biasing said engaging member to move into contact with said pushing member such that movement of said pushing member on said bolt body results in movement of said engaging member between the engagement position and the disengagement position; said pushing member having a first potion and a second portion and cooperating with said first, second, and third coupling members to connect said bolt body to said engagement member, said second coupling member being formed with a slot, said pushing member being disposed on said slot of said second coupling member;

a pushbutton device that is in operational contact with said pushing member between a first pushing position, making said first portion to be aligned with said engagement member to allow movement of said latch-bolt, and a second pushing position, moving said pushing member to allow said second portion to be aligned with said engagement member, preventing movement of said latch-bolt; and a driving device including a first drive member disposed in said housing and having a first driving portion, said first driving portion of said first drive member being activated to contact and push said engaging portion of said engaging member so as to move said latch-bolt from the extended position to the retracted position when said engaging member is disposed at the engagement position, contact between said first driving portion of said first drive member and said engaging portion of said engaging member being prevented when said engaging member is disposed at the disengagement position;

wherein said driving device further includes:

a first mounting member disposed in said housing and permitting said first drive member to be disposed thereon;

a second mounting member disposed in said housing;

a second drive member disposed between said first and second mounting members such that said first mounting member is disposed between said first and second drive members;

a third drive member disposed on said second mounting member such that said second mounting member is disposed between said second and third drive members;

a first driving rod extending through either said first or third drive member for driving synchronous rotation of said first and third drive members; and a second driving rod extending through said second drive member for driving rotation of said second drive member.

* * * * *